United States Patent [19]

Harris et al.

[11] Patent Number: 4,686,971
[45] Date of Patent: Aug. 18, 1987

[54] METHOD AND APPARATUS FOR EXTRACTION OF PROSTHESES

[76] Inventors: William H. Harris, 655 Concord Ave., Belmont, Mass. 02178; Dennis W. Burke, 24 Marine Rd., South Boston, Mass. 02127

[21] Appl. No.: 673,131
[22] Filed: Nov. 19, 1984
[51] Int. Cl.$^4$ .............................................. A61F 5/04
[52] U.S. Cl. ............................ 128/92 VT; 128/92 YD
[58] Field of Search .............. 128/92 R, 92 E, 92 EC, 128/303 R, 92 D, 92 XT

[56] References Cited

U.S. PATENT DOCUMENTS

| | | | |
|---|---|---|---|
| 2,590,532 | 3/1952 | Haboush | 128/92 EC |
| 2,702,031 | 2/1955 | Wenger | 128/92 R |
| 3,710,783 | 1/1973 | Jascalevich | 128/20 |
| 4,100,626 | 7/1978 | White | 128/92 C |
| 4,187,841 | 2/1980 | Knutson | 128/92 E |
| 4,222,382 | 9/1980 | Antonsson et al. | 128/92 EC |
| 4,354,832 | 10/1982 | Wallsheim | 433/7 |
| 4,361,141 | 11/1982 | Tanner | 128/92 R |
| 4,399,813 | 8/1983 | Barber | 128/92 EC |
| 4,423,721 | 1/1984 | Otte et al. | 128/92 R |
| 4,459,985 | 7/1984 | McKay et al. | 128/92 EC |
| 4,476,861 | 10/1984 | Dimakos et al. | 128/92 EC |
| 4,531,517 | 7/1985 | Forte et al. | 128/92 EC |

FOREIGN PATENT DOCUMENTS 628912  9/1978  U.S.S.R. .......................... 128/92 R

*Primary Examiner*—C. Fred Rosenbaum
*Assistant Examiner*—C. W. Shedd
*Attorney, Agent, or Firm*—Wolf, Greenfield & Sacks

[57] ABSTRACT

A method and apparatus for extracting a prosthesis, particularly a femoral component of a hip prosthesis, which is embedded in a skeletal bone. The apparatus of this invention includes a hollow housing having a lower bearing surface which bears against the proximal end of the bone surrounding the prosthesis to be extracted, a threaded shaft having one end extending into the housing, means mounted externally of the housing which can be rotated to axially advance the shaft and means disposed on the one end of the shaft disposed within the housing for grasping the prosthesis for extraction thereof. A bearing plate may be provided between the proximal end of the skeletal bone and the bearing surface of the housing to evenly distribute the reaction forces applied by the housing over the exposed surface of the proximal end of the bone, and for a cemented prosthesis, over the exposed bone and cement surfaces. This bearing plate may be provided with any desired angle of slope with respect to the proximal end of the bone. Rotation of the threaded shaft causes a controlled, continuous extraction force to be applied to the component to smoothly and slowly break the bonds between the component and the bone or between the component and cement.

13 Claims, 13 Drawing Figures

U.S. Patent  Aug. 18, 1987  Sheet 1 of 4  4,686,971
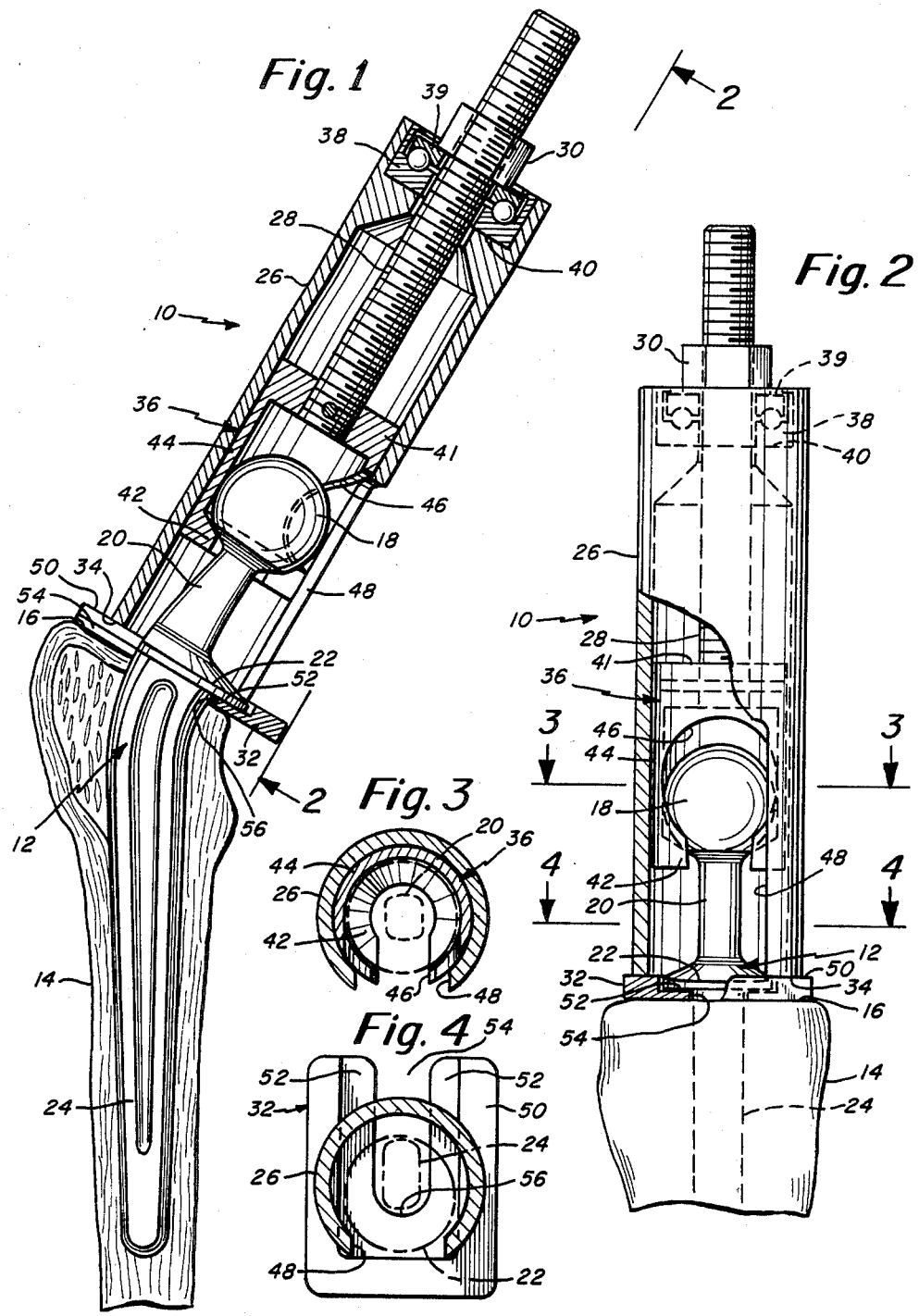

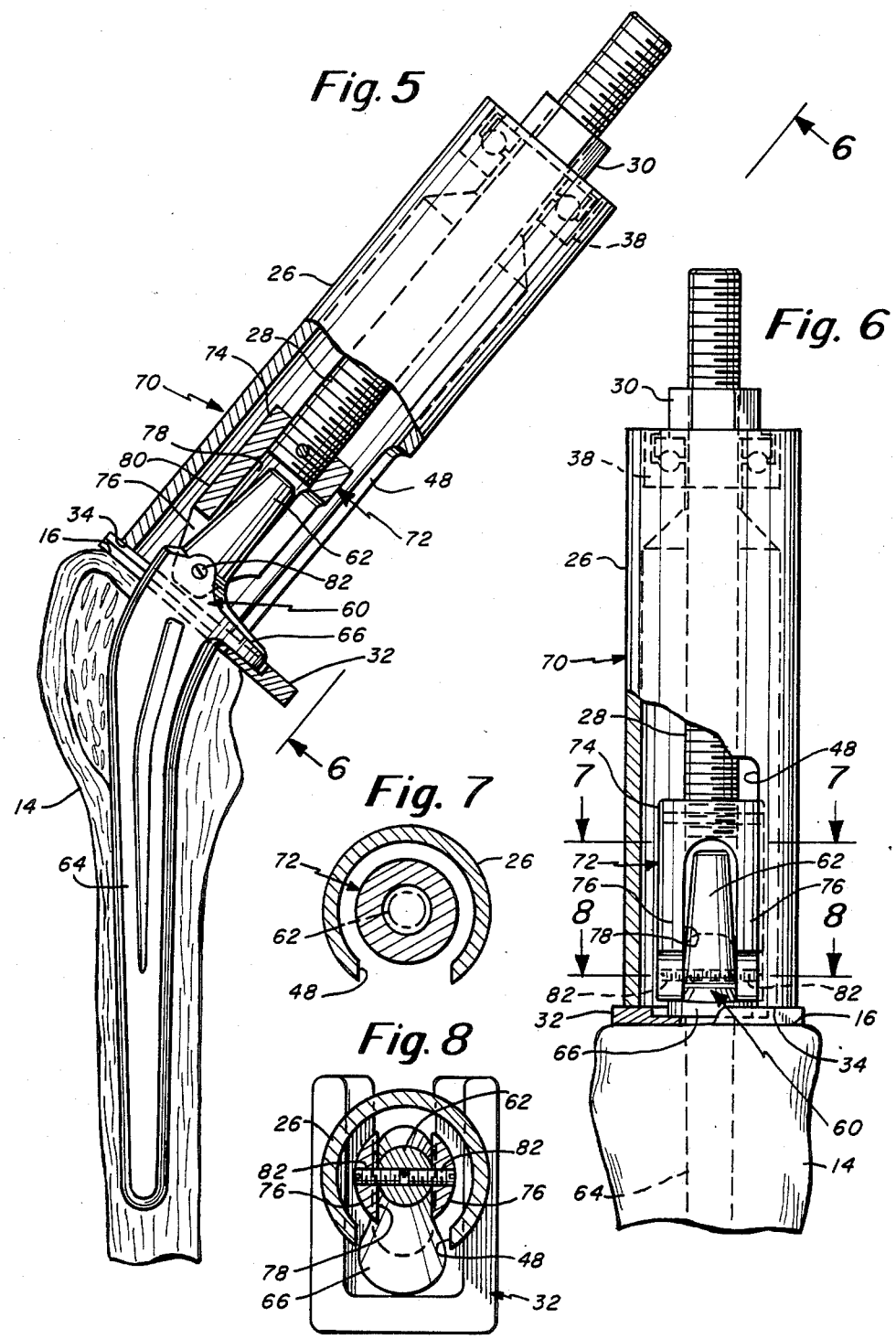

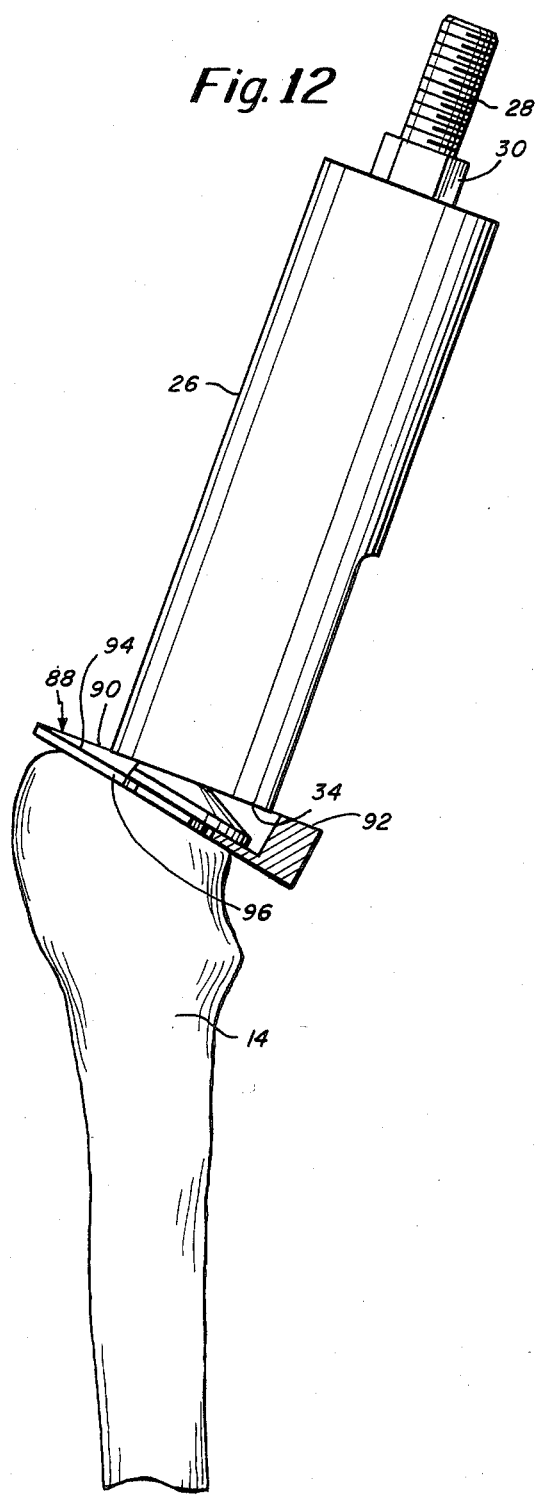
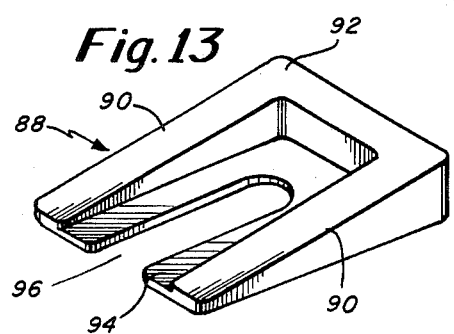

METHOD AND APPARATUS FOR EXTRACTION OF PROSTHESES

FIELD OF THE INVENTION

This invention relates generally to prostheses and more particularly to the surgical extraction of a prosthesis implanted in a skeletal bone.

BACKGROUND OF THE INVENTION

Load-carrying skeletal members, such as the human hip, frequently are rendered non-functional because of fracture, damage, disease, resections for malignancy or disease, pain or malformation. Such members are commonly repaired by a total joint replacement with artificial components, and one type of bone replacement that has been particularly common over the past number of years is that of the human hip. Such hip prostheses typically include a femoral portion or component which is implanted in the femur and an acetabular component which is secured to the pelvis. The femoral component includes a head which rotates in a socket formed in the acetabular component and a stemmed portion which extends into the medullary canal of the femur bone. The head is connected to the stemmed portion by a narrowed, neck portion and a collar is often provided on the stemmed portion which rests in contact with the proximal end of the femur. This femoral head may be permanently secured to or formed integrally with the stemmed portion or the femoral head may be removable from the stemmed portion. Examples of such prostheses are illustrated in the following U.S. Pat. Nos. 4,459,708; 4,406,023; 3,938,198; 3,228,393; 4,038,703; 3,740,769; 3,744,061; 4,012,796; 4,146,936; 4,156,943; 3,808,606; 3,102,536; and 4,080,666. In addition, the following foreign patents disclose known prostheses: German Patent No. 3,003,050; German Patent No. 2,914,454; and British Patent No. 1,446,097.

Many of these known prosthetic devices require the use of cement for embedding the stemmed portion of the femoral component into the medullary canal of the femur. While known cemented systems usually are satisfactory in the short term, various reports of long term results of cemented total hip replacements with a minimum follow up of ten years show that the loosening rate of the femoral component is in the neighborhood of 30% to 50%. (See Moreland, J. R., et al, "Aseptic Loosening of Total Hip Replacement: Incidence and Significance" *In the Hip: Proceedings of the Eighth Open Scientific Meeting of the Hip Society*, pp. 281-291, St. Louis, C. V. Mosby, 1980); Salvatti, E. A., et al, "A Ten Year Follow-Up Study of our First One Hundred Consecutive Charnley Total Hip Replacements", 63 A. J. Bone Joint Surg. 753-767, 1981; Mueller, M. E., "Long Term Follow-Up of Total Hip Replacements", presented at the AOA International Symposium on "Frontiers in Total Hip Replacement", May, 1981, Boston, Mass.; and Coventry, M. B., "Ten Year Follow-Up Study of Total Hip Replacement at the Mayo Clinic", presented at the AOA International Symposium on "Frontiers in Total Hip Replacement", Boston, Mass., May, 1981). Thus, extraction of the femoral component is often required for replacement thereof with a new femoral component.

Because of the problems associated with cemented implants, more recent developments in orthopedic research have been directed toward generating implants which are fixed to the skeleton by bony ingrowth without the use of any cement. Examples of devices utilizing such a bony ingrowth technique are illustrated in U.S. Pat. Nos. 3,314,420; 2,688,139; 3,808,606; and 3,938,198. However, even when bony ingrowth techniques are used, extraction and replacement of the femoral component is often necessary because of changing stresses within the prosthesis and the bone, oversights in the prosthesis design and other factors which may cause dislodgement or premature failure of the implant.

Whether the femoral component is implanted using cement or bony ingrowth techniques, the extraction process is very difficult and dangerous, occasionally resulting in shattering of the femur bone. In some components, such as those illustrated in U.S. Pat. Nos. 4,080,666 and 4,406,023, extraction is facilitated by providing means on the femoral component for attachment of an extractor. Presently, one commonly used method and apparatus for extracting a femoral component is that shown in U.S. Pat. Nos. 4,222,382. U.S. Pat. No. 4,399,813 shows a variation of the apparatus of U.S. Pat. No. 4,222,382 for extracting a broken tip of a femoral component. In the apparatus of U.S. Pat. No. 4,222,382, a sliding weight is utilized to provide an impact shock for breaking the bonds between the component and the bone to allow eventual removal of the component. Forces are applied to the bonds between the component and the bone in a discontinuous manner by the use of a severe jolt or shock. This technique is highly undersirable because of the danger of causing damage to the bone, such as shattering thereof. Another unrelated method of extracting a cemented prosthesis is shown in U.S. Pat. No. 4,248,232.

SUMMARY OF THE INVENTION

An object of this invention is to provide apparatus and a method for extracting prostheses embedded in skeletal bones which overcome the problems and dangers associated with prior art apparatus.

Another object of this invention is to provide apparatus and a method for safely and efficiently extracting the femoral component of a hip prosthesis from a femur bone.

These and other objects of the invention are more clearly appreciated from the following described apparatus and method which permit the extraction of prostheses by the application of a continuous force thereto. This invention has particular applicability to the extraction of a femoral component of a hip prosthesis from a femur bone.

The apparatus of this invention includes a housing, one end of which is provided with a bearing surface which is adapted to rest in a load-bearing relationship with the proximal end of a bone into which the prosthesis is implanted. Extending through a wall of the housing at a point spaced from the bearing surface is a threaded shaft which can be moved axially within the housing by rotation of a threaded nut mounted onto the shaft externally of the housing. Secured to an end of the shaft disposed within the housing is apparatus for grasping one end of the prosthesis projecting from the proximal end of the bone. The grasping apparatus in one embodiment includes a pair of arms provided with set screws which may be driven into the projecting end of the prosthesis. In another embodiment, the grasping apparatus includes a housing with inwardly extending lips which can be slid beneath a laterally extending portion of the prosthesis, such as a femoral head resting on a narrowed neck, to grasp the laterally extending portion from beneath. Rotation of the nut causes a force to be applied to the prosthesis generally along the direction of elongation thereof. This force is applied in a controlled, continuous manner to slowly break the bonds between the component and the bone or the component and cement bonding the component to the bone to minimize any shattering of the bone.

In another embodiment of the invention, a bearing plate may be provided between the bearing surface of the housing and the proximal end of the bone. This bearing plate allows an even distribution over the entire proximal end surface of the bone of the reaction forces applied by the housing against the bone. This bearing plate may be provided with a ramp forming any desired angle with respect to the surface of the proximal end of the bone. This ramp angle may be adjusted to allow the forces applied to the prosthesis to be more precisely directed along the length of the prosthesis to prevent the application of any transverse forces thereto. The bearing plate is slotted and has an open end to allow the plate to be slid between the proximal end of the bone and a collar on the femoral component. In another embodiment, the bearing plate may be secured to the bone by a back plate with spikes which extend into the bone. The back plate is generally rigid, and allows forces applied to the proximal end of the bone to be distributed along the length of the bone.

BRIEF DESCRIPTION OF THE DRAWINGS

The objects, advantages and features of this invention will be more clearly appreciated from the following detailed description when taken in conjunction with the accompanying drawings in which:

FIG. 1 is a cutaway, pictorial view of one embodiment of the extraction device of this invention shown in conjunction with a stemmed femoral component implanted into a femur bone;

FIG. 2 is a front view of the device of FIG. 1 taken in the direction of the lines 2—2 of FIG. 1;

FIG. 3 is a cross-sectional view of the device of FIG. 1 along the lines 3—3 of FIG. 2;

FIG. 4 is a cross-sectional view of the device of FIG. 1 along the lines 4—4 of FIG. 2;

FIG. 5 is a partially cutaway, pictorial view of another embodiment of the extraction device of this invention shown in conjunction with a stemmed femoral component implanted into a femur bone;

FIG. 6 is a partially cutaway side view of the device of FIG. 5 taken in the direction of the lines 6—6 in FIG. 5;

FIG. 7 is a cross-sectional view of the device of FIG. 5 along the lines 7—7 of FIG. 6;

FIG. 8 is a cross-sectional view of the device of FIG. 5 along the lines 8—8 of FIG. 6;

FIG. 12 is a partially cutaway, pictorial view of another embodiment of the extraction device of this invention shown in conjunction with a stemmed femoral component implanted into a femur bone; and FIG. 13 is a perspective view of the bearing plate of FIG. 12.

DETAILED DESCRIPTION OF THE PREFERRED EMBODIMENT

Figure 9:
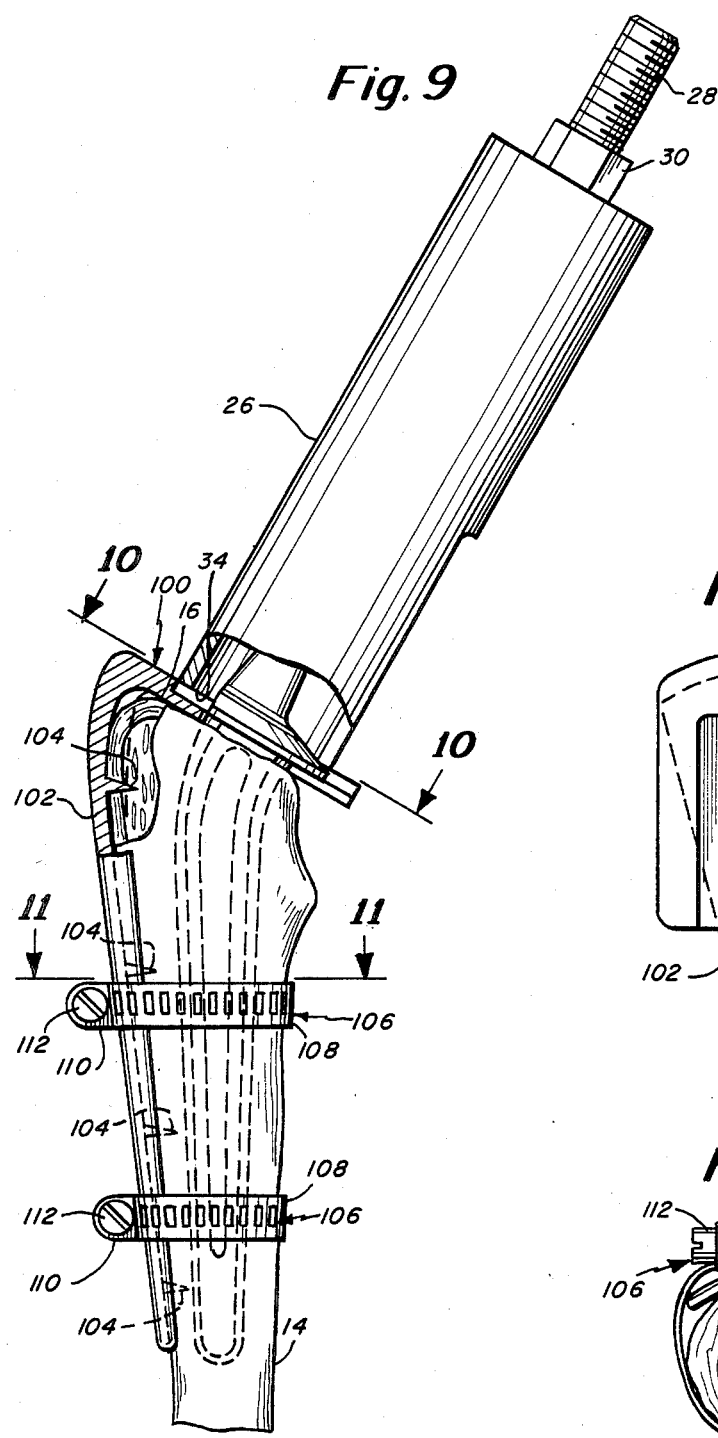
FIG. 9 is a partially cutaway, pictorial view of another embodiment of the extraction device of this invention.

With reference now to the drawings and more particularly to FIGS. 1-4 thereof, extraction device 10 of this invention will be described. FIGS. 1-4 show an exemplary embodiment of the method and apparatus of this invention used to extract a femoral component 12 which is implanted into the medullary canal of a femur bone 14 at the proximal end 16 thereof. Femoral component 12 represents only one exemplary type of hip prosthesis, and this invention is not limited only to extraction of hip prostheses, or only to extraction of prostheses of this or any other particular configuration. Rather, the method and apparatus of this invention may be used to extract prostheses of any configuration implanted into any skeletal bone.

Femoral component 12, as shown in FIG. 1, includes a femoral stem 24 which extends into the medullary canal of the femur 14 from the proximal end 16, a collar 22 which rests on the surface of the proximal end 16 of the femur 14 and a femoral head 18 which is connected to collar 22 by neck 20. Head 18 is adapted to extend into and rotate within a socket formed in an acetabular component (not shown). The extracting device of this invention includes a housing 26, a threaded shaft 28 extending through housing 26 and extractor 36 secured to shaft 28 at its lower end within housing 26.

Housing 26 is provided at its lower end with a bearing surface 34 for resting on and bearing against either a bearing plate 32 (to be described) or proximal end 16 of femur 14 during the extraction of component 12. Opening 48 is disposed in the side wall of housing 26. At the other end of housing 26, spaced from bearing surface 34, there is a thrust bearing 38 which has a rotatable portion 39. Thrust bearing 38 is typically supported by an undercut ledge 40 which extends around the perimeter of the interior of housing 26. Shaft 28 extends into housing 26 through a hole in the center of thrust bearing 38 and is in freely sliding relation therewith. Threadably secured to shaft 28 on the exterior of housing 26 is a nut 30 which rests in direct contact with rotatable portion 39 of thrust bearing 38. Nut 30 may be manually rotated, typically by a wrench, which is not shown for reasons of clarity, to move shaft 28 axially in either direction with respect to housing 26 and thrust bearing 38. Rotation of nut 30 is facilitated by rotatable portion 39 of thrust bearing 38 which rotates in conjunction with nut 30 and with respect to shaft 28.

Non-rotatably secured to a lower end of shaft 28 and disposed within housing 26 is a head extractor 36. Extractor 36 includes upper wall 41 to which the lower end of shaft 28 is secured, side walls 44 and an undercut lip 42 which projects inwardly from the interior of side walls 44, and which extends around most of the perimeter of side walls 44. Disposed on side walls 44 is an aperture 46 which is configured to receive head 18 and a portion of neck 20 of component 12. Typically, aperture 46 has a generally key-hole shape, with the upper portion thereof being enlarged to accept head 18, and the lower portion thereof being narrowed to accept neck 20. Undercut lip 42 resides at least opposite and adjacent the narrowed portion of aperture 46. Lip 42 extends inwardly toward itself a distance such that opposed portions of lip 42 are spaced a distance less than the diameter of head 18 and greater than the thickness of neck 20. Thus, once head 18 passes through aperture 46 and resides within head extractor 36, as head extractor 36 is raised upwardly, away from proximal end 16, undercut lip 42 engages head 18 from the bottom thereof to pull head 18 upwardly. Opening 48 is provided with a size sufficient to allow head 18 and neck 20 of component 12 to pass therethrough and through aperture 46 of extractor 36.

Typically, head extractor 36 and side walls 44 thereof have generally the same configuration as housing 26. However, extractor 36 should have a smaller external dimension than the interior dimension of housing 26, to allow lateral movement of extractor 36 within housing 26 to allow extractor 36 to align itself with respect to head 18. For instance, because of the normal curvature of stem 24 or because of certain problems associated with the surgical technique, housing 26 may not be aligned exactly as desired with respect to neck 20 and head 18, and neck 20 may enter the lower end of housing 26 at an angle. Thus, it is desirable to provide a certain amount of play between extractor 36 and the interior of housing 26 to accommodate this imprecise alignment.

In a preferred embodiment, a bearing plate 32 is provided. Bearing plate 32 rests in contact with proximal end 16 of femur 14 or in contact with proximal end 16 and the cement bonding femoral component 12 to femur 14. Bearing plate 32 is disposed between proximal end 16 and bearing surface 34 of housing 26. Bearing plate 32 may have any desired shape, but is typically rectangular in shape as shown in FIGS. 1-4. Bearing plate 32 includes an outer raised surface 50 upon which bearing surface 34 rests, a slot 54 and a ledge 52 which surrounds slot 54 on three sides. Ledge 52 is recessed below raised surface 50 and is configured to reside between collar 22 and proximal end 16.

Slot 54 is configured to accept the upper portion of stem 24, so that bearing plate 32 may be slid laterally into a position in which stem 24 resides against the upper end 56 of slot 54 and in which ledge 52 is disposed between collar 22 and proximal end 16. Bearing plate 32 may be positioned so that slot 54 is open either to the medial (right side in FIG. 1) or lateral (left side in FIG. 1) sides of femur 14. However, the configuration shown in FIG. 1 is preferred where slot 54 is open to the lateral side of femur 14, since the calcar region of the femur or the medial side is stronger and is more able to sustain the reaction forces applied to it than is the trabeculae on the lateral side of femur 14. When bearing plate 32 is in place, bearing surface 34 rests only on raised surface 50. Generally, resection of a portion of the proximal end 16 of femur 14 is required to provide the necessary space for ledge 52 between collar 22 and proximal end 16.

In a preferred embodiment, bearing plate 32 is independent of and not connected in any way to housing 26 to permit movement of housing 26 with respect to bearing plate 32. One reason for this independent arrangement is that, because stem 24 is curved at its upper end, as component 12 is extracted, housing 26 generally must move with respect to proximal end 16 to allow housing 26 to retain the proper alignment with respect to stem 24. As a result, housing 26 tends to slide with respect to bearing plate 32 as component 12 is extracted. Another reason for requiring that housing 26 be independent of bearing plate 32 is that different prostheses often have different stem widths and collar sizes. Bearing plate 32, slot 54 and in particular ledge 52, should be configured to conform to the stem width and collar size of the particular prosthesis being extracted.

The operation of the device of this invention will now be described with reference to FIGS. 1-4. Since collar 22 generally rests in contact with proximal end 16 of femur 14, a portion of proximal end 16 must be resected to provide a space between collar 22 and proximal end 16. Thereafter, bearing plate 32 is slid into position from the medial side of femur 14 (the right side in FIG. 1) so that stem 24 passes through the opening of slot 54 and resides against the upper end 56 thereof against ledge 52. Collar 22 resides above ledge 52 and typically rests thereon. Extractor 36 is lowered by rotation of nut 30 in one direction and extractor 36 is rotated within housing 26 so that aperture 46 thereof is directly aligned with opening 48. Housing 26 is then slid laterally so that head 18 passes through the enlarged portion of aperture 46 and so that neck 20 passes through the narrowed portion of aperture 46 until head 18 resides totally within extractor 36. Housing 26 is placed so that bearing surface 34 rests only in contact with raised surface 50 of bearing plate 32.

Nut 30 is rotated in the other direction, typically by means of a wrench (not shown) to withdraw shaft 28 axially upwardly from housing 26. Nut 30 rests in contact with rotatable portion 39 of thrust bearing 38 which rotates therewith to facilitate the movement of shaft 28 and the rotation of nut 30. As shaft 28 moves axially through the opening of thrust bearing 38, lip 42 rises upwardly until it is contact with the underside of head 18. Thereafter, continued rotation of nut 30 applies a force upwardly generally parallel to the direction of elongation of stem 24 of component 12. The amount of the force applied can be controlled by adjusting the force applied by the wrench to nut 30. Initially, this force applied to shaft 28 and thus to stem 24 serves only to break the bonds existing between stem 24 and the interior of the medullary canal of femur 14, if the bonds are the result of tissue ingrowth into stem 24. If stem 24 is cemented into the femur 14, the applied force breaks the bonds between stem 24 and the cement. Most of this force is a shearing force applied to the cement bond or bony ingrowth, and not to the femur bone. The reactive force is transmitted from housing 26 through bearing surface 34 to bearing plate 32, where it is distributed evenly over the proximal end 16 of femur 14, or over the proximal end 16 and the exposed cement surfaces. This force is a steady and a continuous force. As a result, little trauma occurs with respect to the bone, and the likelihood of the bone shattering is significantly reduced.

As the bonds begin to break, the stem will begin to rise upwardly out of femur 14, and nut 30 must be rotated an additional amount to withdraw shaft 28 further. As stem 24 rises out of femur 14, housing 26 tends to slide along bearing plate 32, because the position of head 18 tends to move. Because stem 24 generally is tapered downwardly towards its lower tip, once component 12 has been lifted a short distance out of femur 14, and once the bonds have been broken, component 12 generally can be thereafter removed manually without the need of device 10.

Another embodiment of the extractor device 70 of this invention will now be described with reference to FIGS. 5-8, and, for purposes of illustration only, in conjunction with an exemplary femoral component 60 having a stem 64, a neck 62 and a collar 66. Like numbers will be used for like parts where possible. The embodiment of FIGS. 5-8 is for use with prostheses which have a removable head or no head. For example, in femoral component 60, the head (not shown) is not secured to neck 62. Rather, neck 62 extends into an aperture within the head. In this particular embodiment, the head is removed prior to the extraction of component 60. As in the embodiment of FIGS. 1-4, stem 64 of component 60 resides within the medullary canal of a femur bone 14. In this embodiment, the configuration of device 70 is identical in almost every respect to the configuration of device 10, except for extractor 72. Device 70 includes a housing 26 having an opening 48, a thrust bearing 38 disposed in one end of housing 26, a shaft 28 extending through thrust bearing 38, a nut 30 threadably disposed on shaft 28 externally of housing 26 to provide movement of shaft 28 with respect to housing 26 and a bearing surface 34 resting in contact either with a bearing plate 32 or proximal end 16 of femur 14.

Secured to the lower end of shaft 28 within housing 26 is extractor 72. Extractor 72 includes an upper portion 74, two fingers 76 and a rear wall 80. Upper portion 74 is secured to the lower end of shaft 28, and the two laterally spaced fingers 76 extend downwardly from upper portion 74 and define a cavity 78 therebetween. Rear wall 80 bounds one part of cavity 78 between fingers 76. Fingers 76 are spaced a distance equal to or greater than the width or diameter of neck 62 so that cavity 78 can accept neck 62. One set screw 82 is threaded into the lower end of each finger 76, and the two screws 82 are positioned directly opposite one another. Set screws 82 are adapted to be screwed into corresponding pre-existing or newly drilled holes in neck 62 to pivotally couple neck 62 to extractor 72.

The operation of the embodiment of FIGS. 5-8 will now be described. First, a bearing plate 32 is slid into position, in the manner described with respect to FIGS. 1-4. Thereafter, nut 30 is rotated in one direction to move shaft 28 axially toward housing 26 to drive extractor 72 through housing 26 and out the end thereof adjacent bearing surface 34, so that set screws 82 are exposed. Cavity 78 is aligned with opening 48, and housing 26 is slid laterally so that neck 62 passes through opening 48 and into cavity 78. Set screws 82 are aligned with corresponding holes in neck 62 and then are screwed into the holes in neck 62. The holes in neck 62 may either be pre-existing, or be newly drilled just prior to this procedure. After set screws 82 have been screwed into neck 62, extractor 72 and neck 62 are pivoted with respect to one another about set screws 82 to provide the required alignment of housing 26 with respect to neck 62. This pivotal connection between neck 62 and extractor 72 allows device 70 to extract any such component, regardless of the angle at which neck 62 projects from the proximal end 16 of femur 14.

Thereafter, nut 30 is rotated in the opposite direction to move shaft 28 axially away from proximal end 16 and to withdraw extractor 72 into housing 26 and away from proximal end 16. Continued rotation of nut 30 applies the desired upward force on component 60 to break the cement or bony ingrowth bonds to permit withdrawal of component 60, as previously described for FIGS. 1-4. The pivotal connection between neck 62 and extractor 72 also allows device 70 to accommodate the movement of neck 62 as component 60 is withdrawn, and as device 70 slides along bearing plate 32.

Another embodiment of the bearing plate is shown in FIGS. 12 and 13 for use with either device 10 or device 70. Bearing plate 88 includes raised surfaces 92, ramps 90, ledge 94 and slot 96. In this embodiment, raised surfaces 92 include angled ramps 90 which form an acute angle with respect to ledge 94. One ramp 90 is disposed on each side of the neck of the component or on each side of slot 96. Ramps 90 may be formed unitary with plate 88, or ramps 90 may be removable therefrom to form flat raised surfaces as in plate 32. If ramps 90 are removable, they are typically provided with pegs (not shown) which extend into corresponding holes disposed in plate 88 to secure ramps 92 to plate 88 to prevent ramps 90 from sliding or otherwise moving with respect to plate 88 during the extraction operation.

Ramps 90 provide an acute angle with respect to proximal end 16 and ramps 90 slopes upwardly towards the medial side of femur 14 (right side of FIG. 12). Bearing surface 34 of housing 26 rests directly on ramps 90, and thus by selection of the desired angle for ramps 90 the angle which housing 26 assumes with respect to either component 12 or component 60 during the extraction process may be controlled. It is desirable that the extracting forces provided by extractors 36 and 72 be in a direction which is generally parallel to the upper portion of components 12 and 60 to minimize the lateral forces applied thereto during the initial stages of the extraction process to reduce the chances of shattering the femur. The precise angle of ramps 90, and thus the precise angle of housing 26 depends upon the configuration of components 12 or 60 and the amount and angle of curvature thereof, and upon the particular femur shape. The angle provided by ramps 90 should be adjusted for each particular component, and for each particular femur. For this purpose, removable ramps of varying angles could be provided with each bearing plate, so that the physician could select the preferred angle in each instance.

Figure 10:
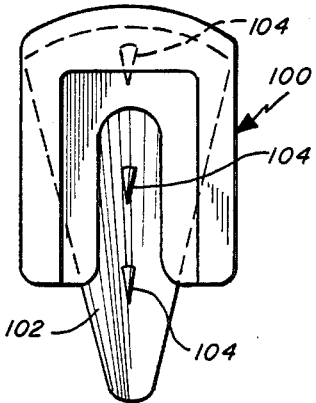
FIG. 10 is a top view of the device of FIG. 9 along the lines 10—10 of FIG. 9 in the direction shown by the arrows.
Figure 11:
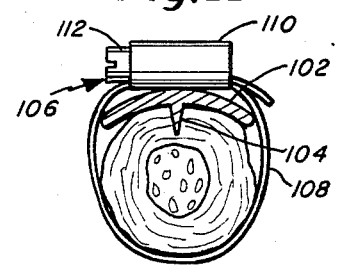
FIG. 11 is a cross-sectional view of the device of FIG. 9 along the lines 11—11 of FIG. 9.

Another embodiment of the bearing plate of this invention is shown in FIGS. 9-11. The bearing plate 100 shown in FIGS. 9-11 is particularly suitable for use with components which are embedded in bones in which the proximal end thereof cannot sustain the reaction forces resulting from the withdrawal of the component from the bone. Examples include situations where the bone, especially the proximal end thereof, is weakened due to osteoporosis, or where the bone has been damaged or reduced in size because of previous implantations and extractions of prostheses and there is not sufficient bone surface remaining to withstand the forces applied thereto. The embodiment of FIGS. 9-11 can be used in conjunction with any of the previously described embodiments of this invention. This embodiment of FIGS. 9-11 is again described in conjunction with an exemplary femoral component, for purposes of illustration only.

In FIGS. 9-11, a bearing plate 100 is provided which resides between bearing surface 34 of housing 26 and proximal end 16 of femur 14. Secured to the back portion of bearing plate 100 at one end thereof is a relatively rigid back plate 102 which is adapted to extend downwardly along a portion of the lateral side (left side in FIG. 9) of femur 14. Back plate 102 is provided with a plurality of spikes 104 which are driven into the lateral surface of femur 14. Plate 102 and spikes 104 are held in position by clamps 106. Clamps 106 may be any suitable clamp. An exemplary clamp is shown in FIG. 9 to include a slotted metal band 108 and a tightening mechanism 110. The circumferential length of band 108 is adjusted by rotation of a screw 112 in tightening mechanism 110 whose threads engage the slots in band 108, in a manner known to those skilled in the art. The number of clamps 106 which are utilized depends upon the length of plate 102, which in turn depends upon the amount of bone surface available and the strength of the bone adjacent proximal end 16 of femur 14.

The dimensions of housing 26 and of extractors 36 and 72 depend upon the size and configuration of the component to be extracted. Housing 26 may be of any desired shape or size, so long as it provides sufficient support for shaft 28 and a bearing surface 34 for bearing against the proximal end 16 of femur 14 or against bearing plate 32. In the embodiment shown in FIGS. 1-13, housing 26 preferably has a cylindrical shape. Similarly, the size and shape of bearing plate 32, and of slot 54 and ledges 52 are each a function of the size of the stem and the size and configuration of the collar, as previously indicated. The size of aperture 46 and of lip 42, and the size and spacing of fingers 76 are also a function of the size and shape of the particular component to be extracted. Shaft 28 typically has a one half inch diameter, and has twenty threads to the inch. However, other shafts with different sizes and thread configurations would be suitable. The primary requirement for shaft 28 is that it be capable of providing the desired mechanical advantage and of withstanding excessive forces. Typically, all of the components of this invention are formed of some form of stainless steel, or of other hardened materials capable of withstanding the extreme forces encountered. Housing 26 should be formed of a suitable material and be of suitable thickness and strength so that it does not buckle upon the application of force during removal of the component.

The above described extraction device provides a controlled, continuous and smooth force to the component which may, without trauma, break the bond between the component and the bone, or between the component and the cement. In addition, the angle at which the force is applied to the component may be adjusted to optimize the bond breaking effect and to minimize any chance of fracturing the bone during the extraction process. Furthermore, the extraction device of this invention allows the smooth and rapid withdrawal of the component from the bone with a minimum of discomfort to the patient. This device is suitable for use with any component, whether or not the bone is diseased or is in otherwise weakened condition.

Although this invention has been described only with regard to an exemplary embodiment for extracting the femoral component of a hip joint replacement, the same principles may also be applied to elbow and shoulder joint replacements.

Modifications and improvements will occur within the scope of this invention to those skilled in the art, and the above description is intended as exemplary only. The scope of this invention is defined only by the following claims and their equivalents.

What is claimed is:

1. Apparatus for extracting the stemmed component of a prosthesis from a bone in which it is implanted, said apparatus comprising:
   a housing having a first end and a bearing surface disposed at a second thereof spaced from said first end, said bearing surface being adapted to bear against a proximal end of the bone surrounding the prosthesis;
   a shaft slidably and nonrotatably disposed with respect to said housing, said shaft having a first end disposed within said housing;
   means disposed on said first end of said shaft for grasping the stemmed component; and
   means threadably coupled to said shaft and adapted to be rotated with respect to said shaft for axially moving said shaft with respect to said second end of said housing and for applying a continuous, controlled force to the stemmed component directed away from the proximal end of the bone generally in the direction of elongation of the component to pull the component away from the bone when the component is grasped by said grasping means.

2. A device for extracting a stemmed femoral component from a femur bone, the stemmed femoral component having a neck projecting from the proximal end of the bone and an enlarged head disposed on an end of the neck spaced from the proximal end of the bone, said device comprising:
   an elongated housing having a lower surface for transmitting a force to the proximal end of the femur and an upper end spaced from said lower surface;
   a bearing plate disposed between the proximal end of the femur and said lower surface of said housing and surrounding the neck of the stemmed component on three sides thereof, one surface of the bearing plate being in contact with the proximal end of the femur and another surface of the bearing plate being in contact with said lower surface of said housing;
   an elongated shaft extending through said upper end of said housing and having a first end disposed in the interior of said housing;
   means connected to said first end of said shaft within said housing for grasping said stemmed femoral component, said grasping means having an undercut lip adapted to surround the neck of the component and to grasp the head of the component on a side thereof facing the proximal end of the femur; and
   means for advancing the shaft away from the proximal end of the femur to cause said undercut lip to grasp the head of the femoral component and to extract the femoral component from the femur bone.

3. A device for extracting a stemmed femoral component from a femur bone, the stemmed component having a neck portion projecting from the proximal end of the femur, said device comprising:
   an elongated housing having a lower surface for transmitting a force to the proximal end of the femur and an upper end spaced from the lower surface;
   a bearing plate disposed between said lower surface of said housing and the proximal end of the femur, said bearing plate surrounding the neck portion of the femoral component on three sides thereof and having one surface on contact with the proximal end of the femur and another surface in contact with said lower surface of said housing;
   an elongated shaft extending through said upper end of said housing and having a first end disposed within the interior of said housing;
   spaced fingers attached to said first end of said shaft and extending toward the proximal end of the femur for receiving the neck portion of the femoral component therebetween;

means disposed on said spaced fingers for securing said fingers to the neck portion of the femoral component; and means for advancing said shaft away from the proximal end of the femur to extract the femoral component from the femur.

4. A method for extracting the stemmed component of a prosthesis from a bone in which it is implanted, said method comprising the steps of:

attaching a portion of the stemmed component projecting from a proximal end of the bone to a threaded shaft;

supporting the shaft in a housing which has a lower end bearing against the proximal end of the bone; and advancing the shaft axially away from the proximal end of the bone in a direction generally parallel to the direction of elongation of the stemmed component by rotation with respect to the shaft of means threadably coupled to the shaft, the shaft being generally nonrotatable with respect to the housing, the threadably coupled means bearing against a portion of the housing spaced from the lower end of the housing.

5. The method as recited in claim 4 further comprising the step of evenly distributing bearing forces applied to the proximal end of the bone by the lower end of the housing over most of the exposed surface of the proximal end of the bone.

6. Apparatus for extracting the stemmed component of a prosthesis from a bone in which it is implanted, said apparatus comprising:

a housing having a first end and a bearing surface disposed at a second end thereof spaced from said first end, said bearing surface being adapted to bear against a proximal end of the bone surrounding the prosthesis;

a shaft slidably disposed with respect to said housing, said shaft having a first end disposed within said housing;

means disposed on said first end of said shaft for grasping the stemmed component;

means for axially moving said shaft selectively with respect to said second end of said housing and for applying a continuous, controlled force to the stemmed component directed away from the proximal end of the bone generally in the direction of elongation of the component to pull the component away from the bone when the component is grasped by said grasping means; and a bearing plate disposed between said bearing surface of said housing and the proximal end of the bone.

7. The device as recited in claim 6 wherein said bearing plate is in unsecured relation to said housing.

8. The device as recited in claim 6 wherein said bearing plate comprises:

a raised surface on one side thereof adapted to receive said bearing surface of said housing thereagainst;

a lip recessed below said raised surface and adapted to surround on three sides a portion of the stemmed portion of the prosthesis projecting from the bone; and a second surface on a side of said bearing plate opposite of said raised surface adapted to rest on the proximal end of the bone.

9. The device as recited in claim 8 wherein said raised surface is angularly disposed with respect to said second surface.

10. The device as recited in claim 6 further comprising:

a back plate secured at one end to one edge of said bearing plate and extending away from said bearing plate generally in the direction of elongation of the bone;

spikes disposed on said back plate for extending into the bone to secure the back plate to the bone; and means for clamping said back plate to the bone.

11. Apparatus for extracting the stemmed component of a prosthesis from a bone in which it is implanted, said apparatus comprising:

a housing having a first end and a bearing surface disposed at a second end thereof spaced from said first end, said bearing surface being adapted to bearing against a proximal end of the bone surrounding the prosthesis;

a shaft slidably disposed with respect to said housing, said shaft having a first end disposed within said housing;

means disposed on said first end of said shaft for grasping the stemmed component, said grasping means comprising:

side wallls having an aperture formed therein adapted to accept an enlarged portion of the component projecting from the bone; and undercut lips extending inwardly toward each other from the side walls for grasping the enlarged portion of the component from beneath between the enlarged portion of the component and the bone; and means for axially moving said shaft selectively with respect to said second end of said housing and for applying a continuous, controlled force to the stemmed component directed away from the proximal end of the bone generally in the direction of elongation of the component to pull the component away from the bone when the component is grasped by said grasping means.

12. Apparatus for extracting the stemmed component of a prothesis from a bone in which it is implanted, said apparatus comprising:

a housing having a first end and a bearing surface disposed at a second end thereof spaced from said first end, said bearing surface being adapted to bear against a proximal end of the bone surrounding the prosthesis;

a shaft slidably disposed with respect to said housing, said shaft having a first end disposed within said housing;

means disposed on said first end of said shaft for grasping the stemmed component, said grasping means comprising:

a pair of gnerally parallel, straight, spaced fingers extending away from said first end of said shaft and adapted to capture therebetween a portion of the component projecting from the bone, said fingers extending generally parallel to said shaft along the entire length of said fingers; and means for mechanically coupling each finger to a portion of the stemmed component projecting from the bone; and means for axially moving said shaft selectively with respect to said second end of said housing and for applying a continuous, controlled force to the stemmed component directed away from the proximal end of the bond generally in the direction of elongation of the component to pull the component away from the bone when the component is grasped by said grasping means.

13. Apparatus for extracting the stemmed component of a prosthesis from a bone in which it is implanted, said apparatus comprising:
- a housing having a first end and a bearing surface disposed at a second end thereof spaced from said first end, said bearing surface being adapted to bear against a proximal end of the bone surround the prosthesis;
- a shaft slidably disposed with respect to said housing, said shaft having a first end disposed within said housing;
- means disposed on said first end of said shaft for grasping the stemmed component;
- a nut threadably coupled to said shaft; and
- means for rotating said nut with respect to said shaft for axially moving said shaft selectively with respect to said second end of said housing and for applying a continuous, controlled force to the stemmed component directed away from the proximal end of the bone generally in the direction of elongation of the component to pull the component away from the bone when the component is grasped by said grasping means.

* * * * *